US 8,478,422 B2

(12) United States Patent
Epstein et al.

(10) Patent No.: US 8,478,422 B2
(45) Date of Patent: Jul. 2, 2013

(54) ELECTRICAL STIMULATION OF CELL AND TISSUE GROWTH WITH TWO-AND THREE-DIMENSIONALLY PATTERNED ELECTRODES

(75) Inventors: Arthur J. Epstein, Bexley, OH (US); Stephen E. Feinberg, Ann Arbor, MI (US); Derek J. Hansford, Columbus, OH (US); Yanyin Yang, Ellicott City, MD (US)

(73) Assignees: The Ohio State University, Columbus, OH (US); The Regents of the University of Michigan, Ann Arbor, MI (US)

( * ) Notice: Subject to any disclaimer, the term of this patent is extended or adjusted under 35 U.S.C. 154(b) by 739 days.

(21) Appl. No.: 11/992,455

(22) PCT Filed: Sep. 21, 2006

(86) PCT No.: PCT/US2006/036767
§ 371 (c)(1),
(2), (4) Date: Feb. 16, 2010

(87) PCT Pub. No.: WO2007/035849
PCT Pub. Date: Mar. 29, 2007

(65) Prior Publication Data
US 2010/0160999 A1     Jun. 24, 2010

Related U.S. Application Data

(60) Provisional application No. 60/719,236, filed on Sep. 21, 2005.

(51) Int. Cl.
*A61N 1/32* (2006.01)
*A61N 1/04* (2006.01)

(52) U.S. Cl.
USPC .............. 607/66; 607/46; 607/73; 607/50

(58) Field of Classification Search
USPC ............... 607/5, 46, 66, 73, 76, 50, 2, 3
See application file for complete search history.

(56) References Cited

U.S. PATENT DOCUMENTS

| | | | | |
|---|---|---|---|---|
| 4,390,023 A | * | 6/1983 | Rise | 607/66 |
| 5,137,817 A | * | 8/1992 | Busta et al. | 435/207 |
| 5,328,376 A | * | 7/1994 | West | 439/65 |
| 6,148,233 A | * | 11/2000 | Owen et al. | 607/5 |

* cited by examiner

*Primary Examiner* — Carl H Layno
*Assistant Examiner* — Jon Eric C Morales
(74) *Attorney, Agent, or Firm* — MacMillan, Sobanski & Todd, LLC

(57) ABSTRACT

The present invention is generally directed to a method for regulating cellular and tissue physiology, a device for practicing the method, and a process for fabricating the device. In general the process comprises the steps of providing at least one patterned electrode, providing a least one cell, placing the at least one electrode in electrical communication with the at least one cell, and applying a voltage to the electrode thereby delivering an effective amount of a patterned electric field or current thus regulating the physiology and/or growth of the at least one cell.

38 Claims, 18 Drawing Sheets

| Size | IDE200 | | | IDE100 | |
|---|---|---|---|---|---|
| | -1 | -2 | -3 | | |
| $L_1$(mm) | 15 | 15 | 15 | 10 | 10.7 |
| $L_2$(mm) | 14.6 | 13.4 | 13.2 | 10 | 10.4 |
| $W_1$(µm) | 200 | 200 | 200 | 100 | 50 |
| $W_2$(µm) | 1800 | 800 | 250 | 300 | 300 |
| $W_3$(µm) | 700 | 700 | 700 | 450 | 450 |
| H(µm)* | 0.4~0.8 | | | | |
| N** | 4 | 7 | 13 | 15 | 15 |

*H, thickness of the IDE pattern made of SPAN
**N, number of IDE fingers in each electrode

ELECTRICAL STIMULATION OF CELL AND TISSUE GROWTH WITH TWO-AND THREE-DIMENSIONALLY PATTERNED ELECTRODES

RELATED APPLICATIONS

This application claims priority to U.S. Provisional Patent Application No. 60/719,236, filed Sep. 21, 2005.

FIELD OF THE INVENTION

The present invention generally relates to a device and method for electrically regulating cellular and/or tissue physiology using a patterned electric field or current. The present invention further relates to a device for carrying out the regulatory method as well as methods for fabricating the device.

BACKGROUND OF THE INVENTION

The effect of electrical stimulation on healing and cell growth has been explored for decades. Clinical studies have shown improved fracture healing by using electric and electromagnetic fields as early as the 1970s. Disk electrodes coupled to the skin via conductive gel have been developed that generate and deliver a broad, noninvasive, capacitively coupled, and uniform electric field to the fracture site. The problem with conventional externally generated fields is that they cannot be directed preferentially to the fracture site, but rather are generally directed to large regions of an organism. Moreover, since the fields produced by conventional external electrodes are ordinary dipole fields the field strength diminishes with distance from the surface of the electrode. Thus, higher powers are required in order to deliver an effective field strength to the target cells.

Other art overcomes this problem by using implantable electrodes to localize the field, thus electrical regulation could be carried out in specific locations more efficiently, i.e. with waveforms having lower amplitudes and/or frequencies. This work used electrodes made from polymer-coated metals such as fluorocarbon-coated steel. However, such electrodes are not biodegradable/bioabsorbable therefore they require an additional surgery to remove them. Thus, the art is deficient in that it lacks an external electrode that is capable of delivering a localized electric field or current. Furthermore, the art lacks a biodegradable/bioabsorbable implantable device for generating therapeutic electric fields and/or currents.

The present invention fills this gap in the art by using patterned electrodes to create fields that are capable of being localized preferentially on the region of the organism where electric field or current delivery is indicated. Moreover, such electrodes can be made from conductive polymers (CP) that are biodegradable/bioabsorbable. Thus, the electrodes of the present invention can be implanted into an organism for therapeutic purposes, without requiring additional surgery to remove the same when the therapy is complete. Accordingly, the present invention fills a substantial gap in the art, and is novel, non-obvious and deserves broad patent protection.

SUMMARY OF THE INVENTION

The present invention generally relates to a method for electrically regulating the physiology of a variety of cell types in vivo or in vitro. More particularly, the present invention relates to a method for up-regulating or down-regulating cellular processes including without limitation cell growth, metabolic processes, biological product production, and tissue healing and regeneration through the use of patterned electrodes, which deliver a patterned electric field. The present invention also relates to a device for carrying out the regulatory method as well as a method for fabricating the device.

The present invention generally relates to a method for regulating cellular and tissue physiology comprising the steps of providing at least one electrode, providing at least one cell, placing the electrode in electrical communication with the at least one cell, and applying a voltage to the electrode thereby delivering an effective amount of a patterned electric field or current to the at least one cell, whereby the patterned electric field or current regulates the physiology or growth of the at least one cell.

The present invention also generally relates to a device for regulating cellular and tissue physiology comprising at least one electrode capable of delivering an effective amount of a patterned electric field or current to a locus where dosing is indicated. Additionally, the present invention relates to a process for fabricating a patterned electrode for regulating cellular and tissue physiology comprising the steps of providing a nonconductive substrate, providing a conductive material, and applying the conductive material to the substrate in a manner that forms a patterned conductive film adhering to the substrate.

DETAILED DESCRIPTION

The present invention generally relates to a method for electrically regulating the physiology of a variety of cell types in vivo or in vitro. More particularly, the present invention relates to a method for up-regulating or down-regulating cellular processes including without limitation growth, metabolic processes, biological product production, and tissue healing and regeneration through the use of patterned electrodes, which deliver a patterned electric field. The present invention also relates to a device for carrying out the regulatory method as well as a method of fabricating the device.

The term electrical communication, as used herein, includes communication of static and dynamic electric fields, electromagnetic radiation, and electric current.

The term electrode, as used herein encompasses both the singular and plural forms. Thus, statements regarding "an electrode" apply equally to a plurality of electrodes.

The term 2-dimensionally patterned electrodes, as used herein, includes a conductive pattern that substantially extends in two mutually orthogonal dimensions that are generally parallel to a non-conductive substrate. Furthermore, although 2-dimensionally patterned electrodes necessarily include a third spatial dimension, such third dimension is merely a thickness.

The term 3-dimensionally patterned electrodes, as used herein, includes a set of 2-dimensionally patterned electrodes that are generally stacked one on top of the other so that their fields superposition. Generally, the stack comprises layers of 2-dimensionally patterned electrodes that can be separated by intervening dielectric layers. Furthermore, the patterned layers can be the same or different patterns, and can be aligned or offset in any of a variety of ways. For instance, the patterns can be rotationally offset by any number of degrees. Alternatively, the patterns can be linearly offset by any appropriate distance. In a still further alternative, the patterns may be offset so that the layers are no longer parallel. Any combination of the foregoing offsets is also within meaning of the term 3-dimensionally patterned electrode as used herein.

Electrically Regulated Processes

Figure 19:
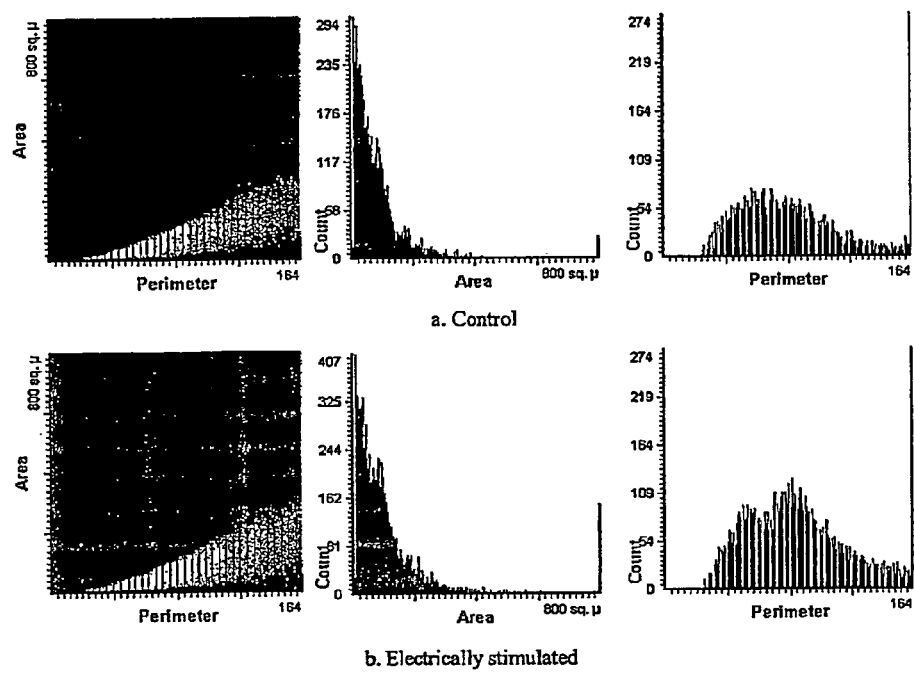
FIG. 19 is a set of plots and a data table showing the effect of applied electric field on cell membrane permeability in a dye uptake study.

According to the present invention subjecting many kinds of cells to a patterned electric field or current enables regulation of a variety of physiological cellular and tissue processes including without limitation stimulating cellular proliferation, healing and/or regeneration. Other examples of physiological processes that can be regulated by the application of a patterned electric field or current include, without limitation, ion channel function, secretory processes, chemical absorption processes, anabolic and catabolic processes, mass transport processes, cell membrane permeability, gene product production, cell division and the like. In one embodiment, cell permeability is increased by applying an electric field of the present invention. An example of this permeability effect can be seen in dye uptake studies as shown in FIG. 19.

The physiological processes of a wide variety of cells and tissues can be regulated by applying a patterned electric field or current. Such cells include, but are not limited to, bone cells including osteoprogenitor and/or stem cells, blood cells, cardiac cells, muscle cells, nerve cells, and skin or vascular cells including epidermal and endothelial cells, respectively.

Although there is a clear relationship between voltage and bone growth, it is not linear. Rather, the rate at which bone growth increases with increasing voltage slows down noticeably at higher voltages. Several plausible explanations exist. Some evidence suggests that as cell concentration increases and, more importantly, as the number of cells adhering to the electrode increases, the field experienced by the bulk cells diminishes due to an screening effect caused by cells at the electrode surface. More particularly, according to this line of reasoning the membranes of the surface-adherent cells insulate the bulk cells from at least a portion of the field. Another explanation may be contact inhibition. That is, when cell density becomes relatively high, the competition for limited sources of nutrients and space causes cell growth to slow even as higher voltages are applied.

According to a third theory, an applied voltage may affect the concentration of cellular growth factors, thereby influencing cellular proliferation. Another theory focuses on the behavior of human cells in response to a pulsed electromagnetic field (PEMF). Still another theory states that the electric field induces expression of one or more growth factors by a mechanism involving the calcium/calmodulin pathway. Another theory says that the field affects voltage-sensitive transmembrane ion channels thereby increasing the influx of calcium ions and triggering a series of events including increased cellular proliferation. Any one of the foregoing theories or any combination thereof can explain why the relationship between bone growth and applied voltage or field strength is non-linear. Regardless of the precise explanation, the relationship between bone healing/regeneration and electrical stimulation is widely recognized.

Electric Fields

Electric fields within the scope of the present invention include, without limitation, constant fields (e.g. DC) including bipolar DC fields, time-varying fields (e.g. AC) and any combination thereof. When AC and DC fields are combined, the DC field's magnitude can be smaller than, equal to, or greater than that of the AC field. Additionally, where AC and DC fields are combined the polarity of the DC field can be varied. Frequency dependant fields can have any of a variety of appropriate wave forms including, but not limited to, square, sinusoidal, triangular, trapezoidal, or more complex patterns. Furthermore, appropriate fields can be inductively coupled, capacitively coupled, and the like. The field can also be pulsed or continuous. Fields within the scope of the present invention can be modulated in any of a variety of ways including temporally and spatially. Preferably, fields within the scope of the present invention can be localized on particular areas of the body so as to preferentially regulate cellular and/or tissue physiological processes in particular locations. More preferably, fields within the scope of the present invention can be localized on individual cells or small collections of cells. In one embodiment field strength can be maximal at the surface of an electrode such as a 2-dimensionally patterned electrode. In another embodiment field strength can be maximal at a distance from the surface of an electrode, such as a 3-dimensionally patterned electrode.

Figure 11:
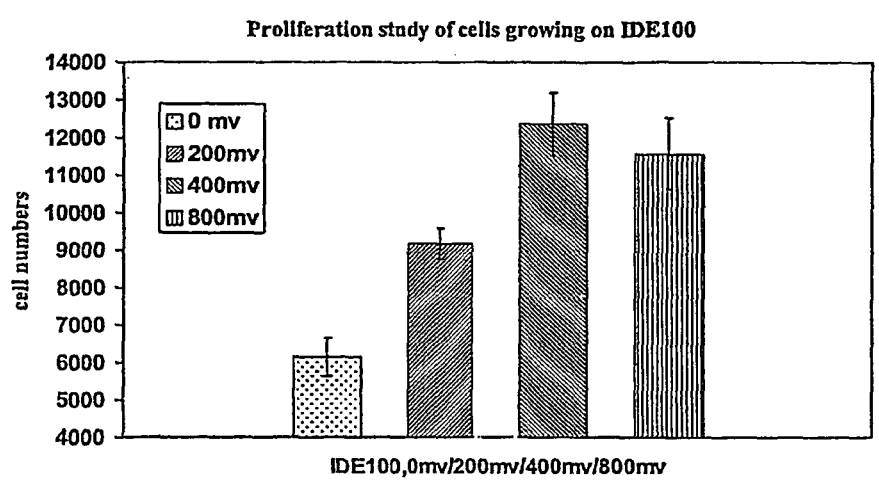
FIG. 11 is a graph showing the voltage dependency of cells growing on IDE 100 under DC electrical stimulation.
Figure 12:
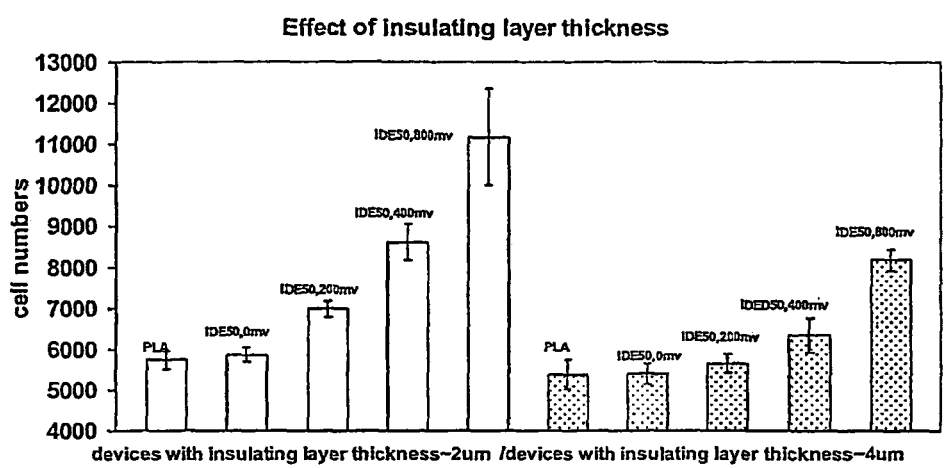
FIG. 12 is a graph showing the relationship between the insulating layer thickness and cell growth on IDE50 under DC electrical stimulation.
Figure 13:
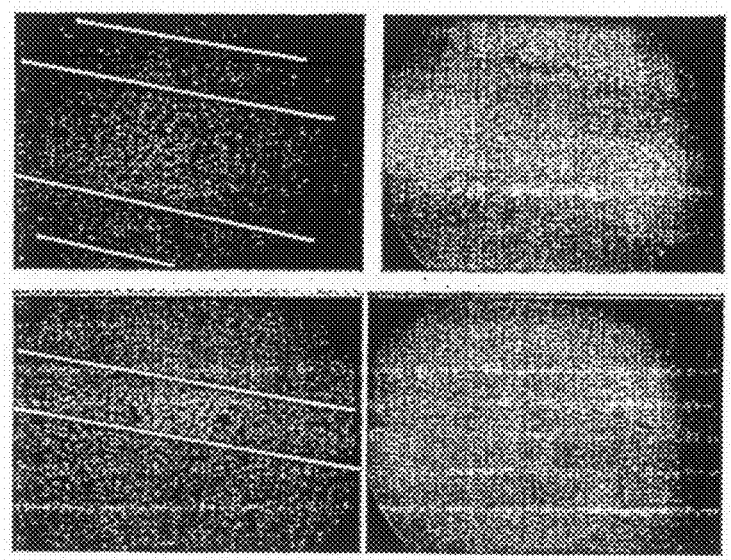
FIG. 13 is a set of images showing the effect of electrical stimulation on distribution of cells grown on IDE 100.

According to the present invention cellular and tissue physiological processes respond differently depending on field strength. In one non-limiting example, higher field strengths tend to result in greater bone growth in terms of proliferation (FIGS. 11 and 12) as well as alkaline phosphatase activity and calcium deposition. However upon a higher voltage, the increase slowed down (FIG. 11), which may be attributed to overconfluence caused contact inhibition or insulating properties of cellular membranes.

Electrodes

Figure 16:
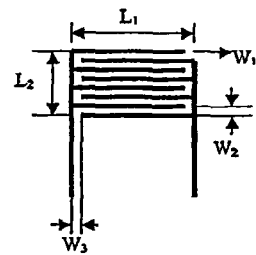
FIG. 16 is a table setting forth the dimensions of several interdigitated embodiments fabricated by printing and in situ polymerization.
Figure 17:
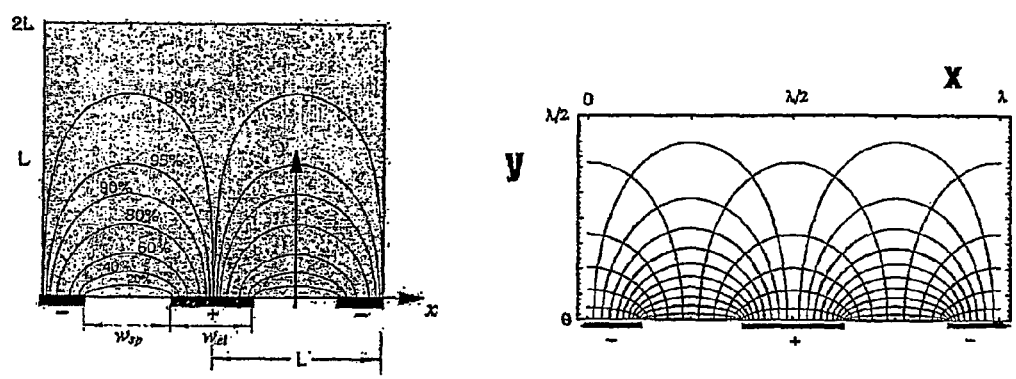
FIG. 17 is a pair of plots showing the isopotential and electric field lines of an example electrode.
Figure 18:
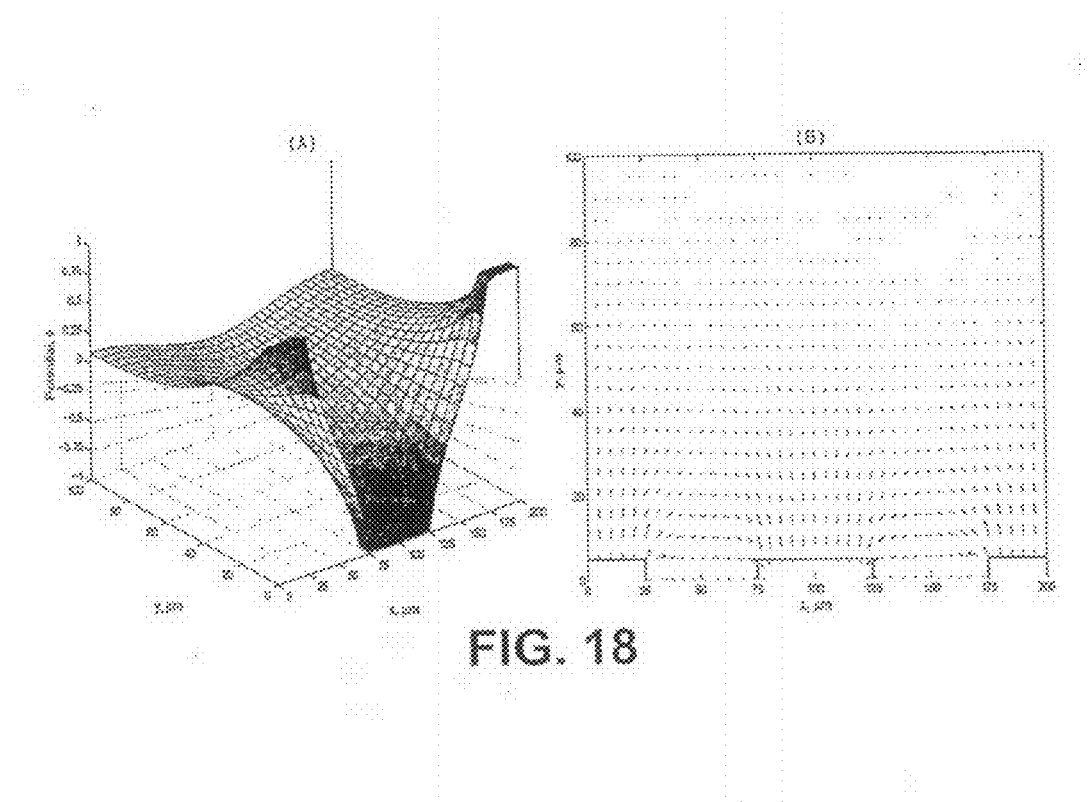
FIG. 18 is a pair of plots showing the potential distribution and electric field lines of an example electrode.

Electrodes within the scope of the present invention can take on any of a variety of appropriate conformations including without limitation 2-dimensionally patterned, and 3-dimensionally patterned electrodes. Patterns within the scope of the present invention include, without limitation, interdigitated designs, parallel lines, concentric circles, or any of a variety of circumscribed regular or irregular shapes. In any case, the sign of the electrode features should alternate in some appropriate manner. For instance, with regard to concentric circles one appropriate manner is that each successive circle has the opposite sign of the one inside and outside of it. In another embodiment, some circles may have the same sign as the circle inside or outside or both inside and outside. The other alternative shapes mentioned above can alternate in a similar manner. For instance, in an interdigitated embodiment, one set of digits is positive and the other set is negative. Some non-limiting examples of interdigitated embodiments are set forth in FIG. 16.

With regard to spacing between the features of 2-dimensionally patterned electrodes, any of a variety of spacings can be appropriate provided the resulting pattern produces a patterned field or current that can be directed to individual cells or small collections of cells. The spacing between pairs of features can be constant across all or a portion of the electrode. Additionally, the spacing can vary from one pair of features to another, and/or along one pair of features. Feature spacings that are within the scope of the present invention include, without limitation, from about 10 nm to about 200 µm. Feature spacings within the scope of the present invention also include, without limitation, from about 100 nm to about 100 µm. Feature spacings within the scope of the present invention also include, without limitation, from about 1 µm to about 100 µm. Feature spacings within the scope of the present invention also include, without limitation, from about 1 µm to about 100 µm.

The feature spacing mentioned above enables the present invention to produce electric fields or currents that are capable of controlling or regulating cellular and/or tissue physiological processes. In general, smaller feature spacings result in finer control over field strength variations. Thus, a smaller feature spacing is required to affect the physiological processes of a single cell than that of a collection of cells. Similarly, different feature spacings can be used to affect the physiological process of cells of different sizes.

As mentioned above, 3-dimensionally patterned electrodes are essentially a set of 2-dimensionally patterned electrodes that are packed in a multilayer fashion so that the field, in a specific location, generated from one layer could be either cancelled or enhanced by the field generated from other layers. This type of electrode pattern enables the present invention to have maximal field strength at a distance from the surface. This is in contrast to 2-dimensionally patterned electrodes, which have maximum field strength at the surface. Thus, 3-dimensionally patterned electrodes produce a patterned electric field or current similar to that of 2-dimensionally patterned electrodes, but also enable the present invention to apply the patterned field at maximum strength to a cell or cells located a distance from the electrode. More particularly, this kind of electrode can be more efficiently used as an external (i.e. non-implanted) electrode. However, 2- and 3-dimensionally patterned electrode can both be either implanted or external.

In one embodiment, a 3-dimensionally patterned electric field can also be generated by simply wrapping the targeted area with the 2-dimensionally patterned electrode.

In addition to 2- and 3-dimensional patterning, the electrode of the present invention can have a controlled surface roughness, which can affect cell adhesion. In general, cells tend to adhere to rougher surfaces better than smoother surfaces. Thus, it may be desirable to include a surface roughness feature in a controlled manner. In one embodiment, surface roughness is produced in a controlled manner by adding a dielectric coating having a textured surface, or by adding a dielectric layer and then creating a texture on the layer, for instance, using a template. In another embodiment surface roughness is achieved by patterning the top dielectric layer in grooves or wells through stamping (soft-lithography).

Electric fields consistent with the present invention can be generated with any of a variety of implantable electrodes, or external electrodes (i.e. not implanted). Such electrodes can comprise any conductive material including without limitation metals and alloys thereof, dielectric-coated metals and metal alloys such as fluorocarbon-coated steel or titanium, doped and/or undoped semiconductors, and doped and/or undoped conductive polymers. In one embodiment, the present invention comprises conductive polymer electrodes. In another embodiment, the present invention comprises bioabsorbable/biodegradable conductive polymer electrodes.

Conducting polymers within the scope of the present invention can be incorporated into the main chain of a copolymer or can be a pendent group or groups of a copolymer. Examples of conductive polymers within the scope of the present invention include without limitation polypyrroles, polythiophenes, and polyanilines. Typically, such conductive polymers are doped in a manner that enhances electrical conductivity for example Poly(3,4-ethylenedioxythiophene) poly(styrenesulfonate) (e.g. Baytron P) and fully sulfonated polyaniline (e.g. NSPAN).

In one embodiment the electrodes of the present invention are fabricated from a self-doped conductive polymer. The meaning of the term self-doped, as used herein, includes conductive polymers wherein the dopant is covalently tethered to the polymer, for instance by a linker group. Self-doped conducting polymers can be used to form electrode patterns that provide a wide range of effective dopant concentrations from about 0.05 to about 1.0 sulfonic acid groups per aniline repeating unit. Additionally, such polymers mitigate diffusion effects that can harm performance.

In one embodiment the electrodes of the present invention are fabricated from sulfonated polyaniline (SPAN). One advantage of SPAN is that introducing $SO_3H$ can improve the water solubility, as well as environmental stability, of polyaniline without substantially sacrificing conductivity. Additionally, the electrical and chemical properties of SPAN are pH independent over a broad range, which is especially important in implantable applications. Furthermore, polyanilines have a wide range of stable oxidations states (including leucoemeraldine, emeraldine, and pemigraniline), a wide selection of inorganic and organic counter ions, and versatile acid-base and redox chemistries. Biomolecules, such as growth factors, hormones, and enzymes, can be incorporated into the conductive polymer electrodes as dopants, thus creating unique properties in addition to biocompatibility and electrical activity.

Figure 1:
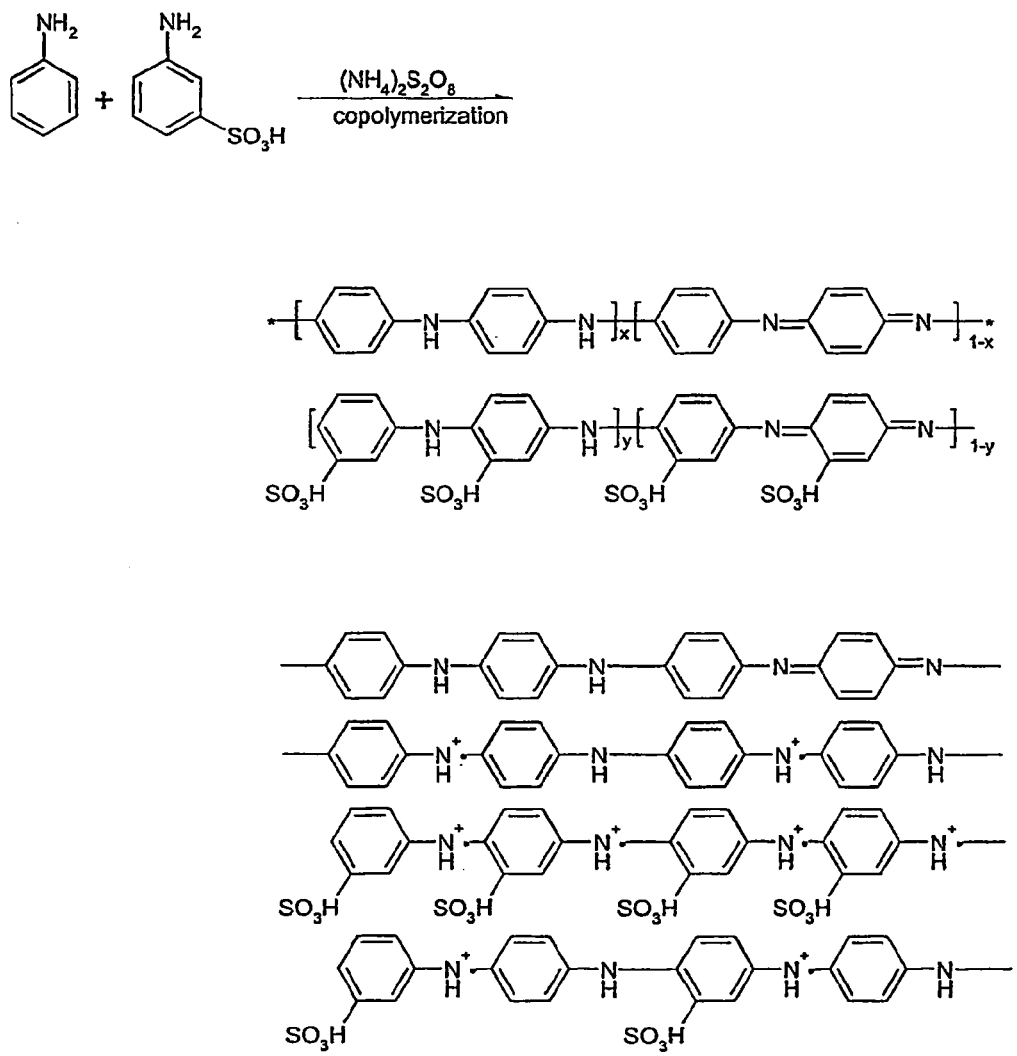
FIG. 1 is a diagram showing a synthetic route to a series of biocompatible conducting polymers (CPs) with different sulfonation ratios.
Figure 15:
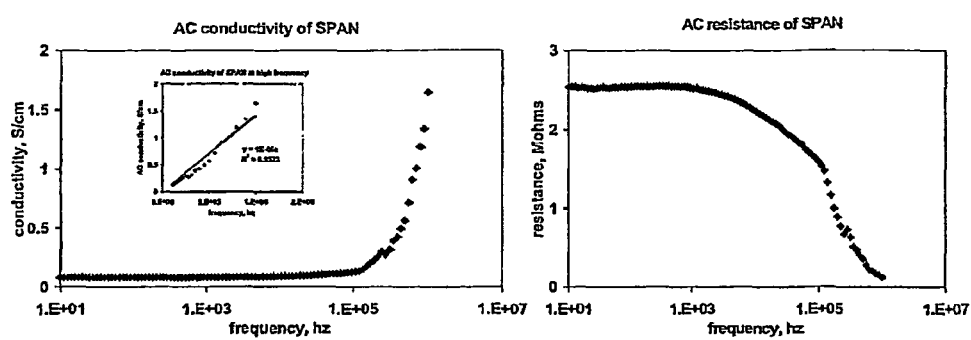
FIG. 15 is a pair of graphs showing the electrical properties of an example SPAN formulation.

Any of a variety of known SPAN preparations can be used in connection with the present invention. For instance, one such preparation can be carried out as follows (See FIG. 1). Aniline, 0.05 mol, is copolymerized with 0.05 mole metanilic acid in 1M HCl with 0.05 mole ammonium persulfate as oxidant. The reaction is kept in ice bath, stirring for about 6 hrs. Then a large excess of acetone is added to precipitate the product, which is collected by filtration. After filtering, washing, and drying the dark green product is ground into powder and dissolved in N-methyl-2-pyrrolidone (NMP) at a concentration of less than 1 wt %. In order to enhance conductivity and ensure electrical continuity, the SPAN film is dip-coated onto a glass slide (2.5 cm×2.5 cm) rather than spin-coated. Excess solvent is removed by drying slowly at room temperature in a fume hood for 48 hours. The resulting film has a thickness of approximately 15±5 μm according to profilometry. The electrical properties of a SPAN formulation is shown in FIG. 15.

TABLE 1

Physical properties of a series of sulfonated polyanilines showing that properties can be adjusted through synthetic modifications.

| Sample # | Monomers* | Oxidant** | Medium | Yield | Solubility | Conductivity (S/cm) |
|---|---|---|---|---|---|---|
| 7305 | AN:MA 0.07 mol:0.03 mol (7:3) | APS 0.05 mol | 0.2 mol HCl/ 200 ml $H_2O$ | 50.73% | insoluble in water, $CH_3Cl$, and toluene. | 0.1 |
| 5505 | AN:MA 0.05 mol:0.05 mol (5:5) | APS 0.05 mol | 0.2 mol HCl/ 200 ml $H_2O$ | 55.46% | Soluble in DMSO, DMF, and NMP. | 0.08 |
| 3705 | AN:MA 0.03 mol:0.07 mol (3:7) | APS 0.05 mol | 0.2 mol HCl/ 200 ml $H_2O$ | 59.86% | Solubility NMP > DMSO≡DMF | 0.005 |
| 5510 | AN:MA 0.05 mol:0.05 mol (5:5) | APS 0.1 mol | 0.2 mol HCl/ 200 ml $H_2O$ | 76.78% |  | 0.003 |

*AN = aniline, MA = metanilic acid
**APS = ammonium persulfate

Table 1 above demonstrates that conductivity can be adjusted by altering monomer ratios.

Patterning and Fabricating

In one embodiment an electrode within the scope of the present invention is fabricated by stamping a solution of conductive polymer or precursor(s) thereof onto an appropriate substrate. Appropriate substrates include without limitation electrically insulating materials. More particularly, such substrates include without limitation metal oxide glasses, ceramics, and organic polymers such as polyethyleneterephthalates, polyolefins, phenolic polymers and the like.

Figure 6:
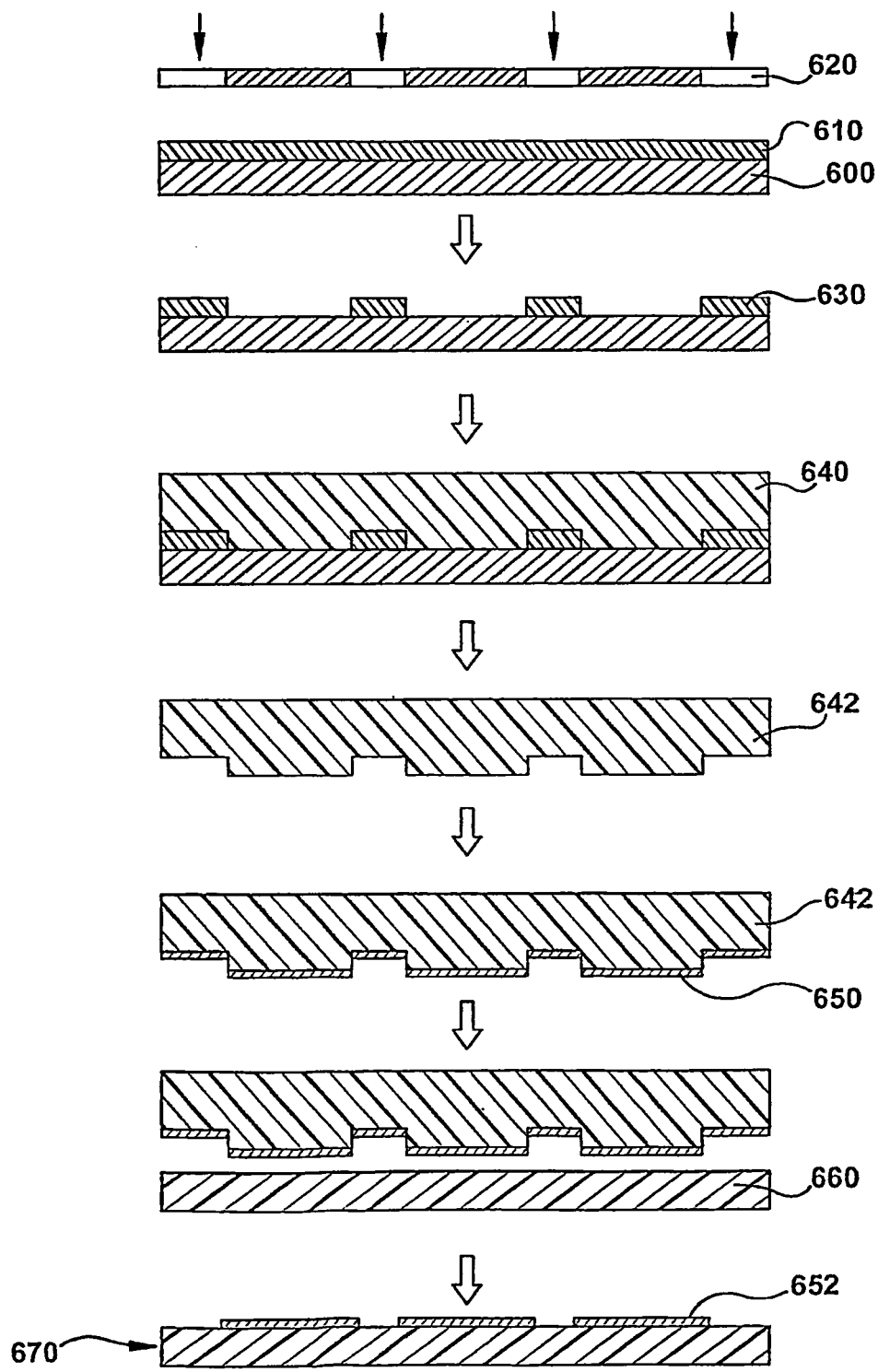
FIG. 6 is an illustration showing the steps of using soft lithography (e.g. stamping) to fabricate a two dimensionally patterned electrode.

Any of a variety of known methods for stamping can be used to fabricate electrodes of the present invention. For instance, in one embodiment a stamp is fabricated as shown in FIG. 6. A substrate 600 is coated with a layer of negative photoresist 610, and is then exposed to UV radiation through an appropriate mask bearing the desired pattern 620. The latent image is developed 630, i.e. the uncrosslinked photoresist is removed, thereby forming a mold. Then a prepolymer 640 is added to the mold, cured, and peeled off. The molded polymer peeled from the mold comprises the stamp 642. The stamp can now be wetted with conductive polymer 650 and/or precursors thereof and applied to an appropriate substrate 660 thereby leaving a stamped image 652, and forming a stamped electrode 670.

Figure 7:
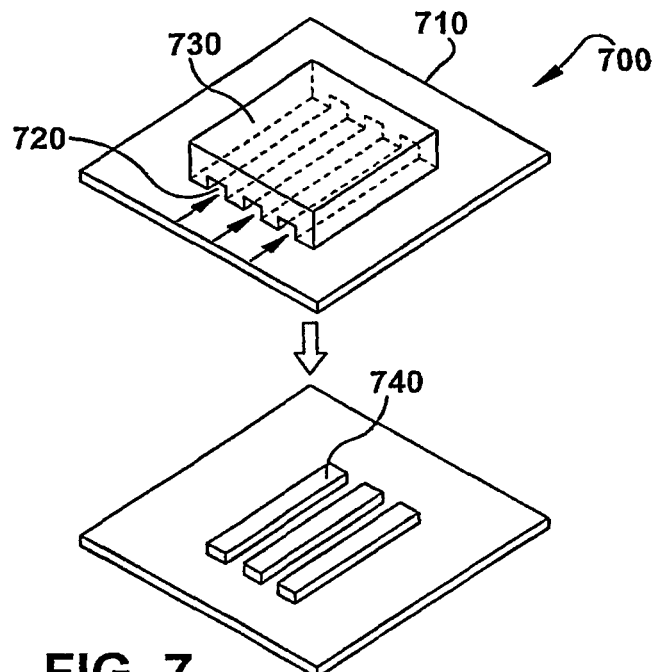
FIG. 7 is an illustration showing the method of micro molding in capillaries (MIMIC)

In another embodiment of the present invention, electrodes can be fabricated using a capillary micromolding technique and/or apparatus 700. More particularly, an empty mold 730 is applied to a substrate 710 so that openings 720 of the mold are exposed as shown in FIG. 7. Then a portion of liquid polymer and/or prepolymer is contacted with the opening. The liquid is drawn into the mold by capillary forces, which distribute the liquid throughout the mold. The liquid is allowed to dry and/or cure and then the mold is removed from the substrate leaving behind a patterned conductive polymer film 740.

In still another embodiment electrodes of the present invention are fabricated by printing conductive polymer and/or prepolymer directly onto an appropriate substrate. In one example an ordinary laser printer is used in combination with specially formulated ink to form a patterned conductive polymer film. An appropriate ink formulation can comprise a conductive polymer and/or prepolymer thereof. Additionally, such an ink may optionally comprise a binder, a surfactant, and/or an oxidizing agent such as ferric ethylbenzene sulfonate. In one example of this embodiment, a substrate coated with an appropriate ink is exposed to excess monomer vapor thereby developing the image in the regions containing oxidizing agent. This results in a conductive polymer image.

Figure 4:
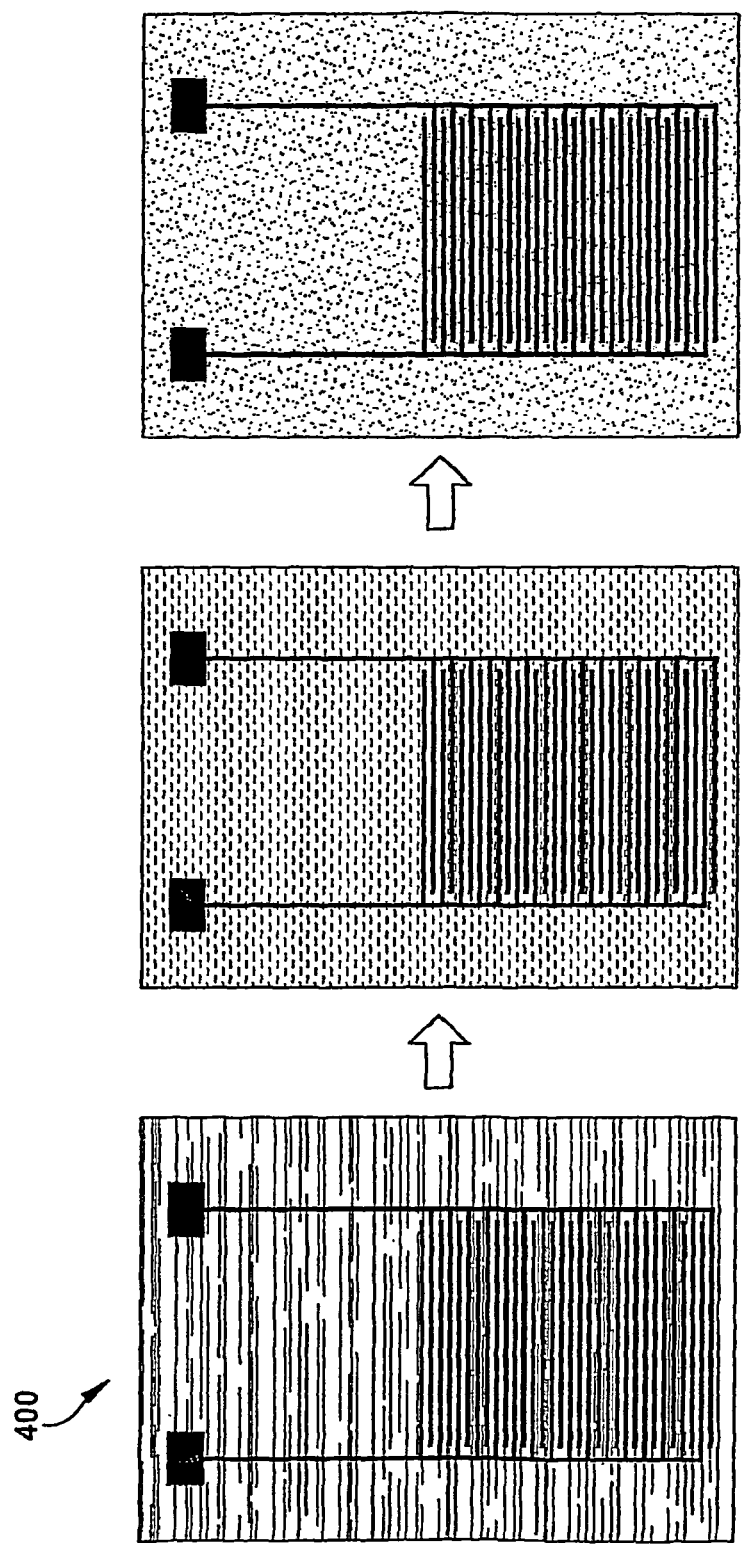
FIG. 4 is an illustration showing the steps of making interdigitated electrodes from conductive polymers by printing and in-situ polymerization.
Figure 5:
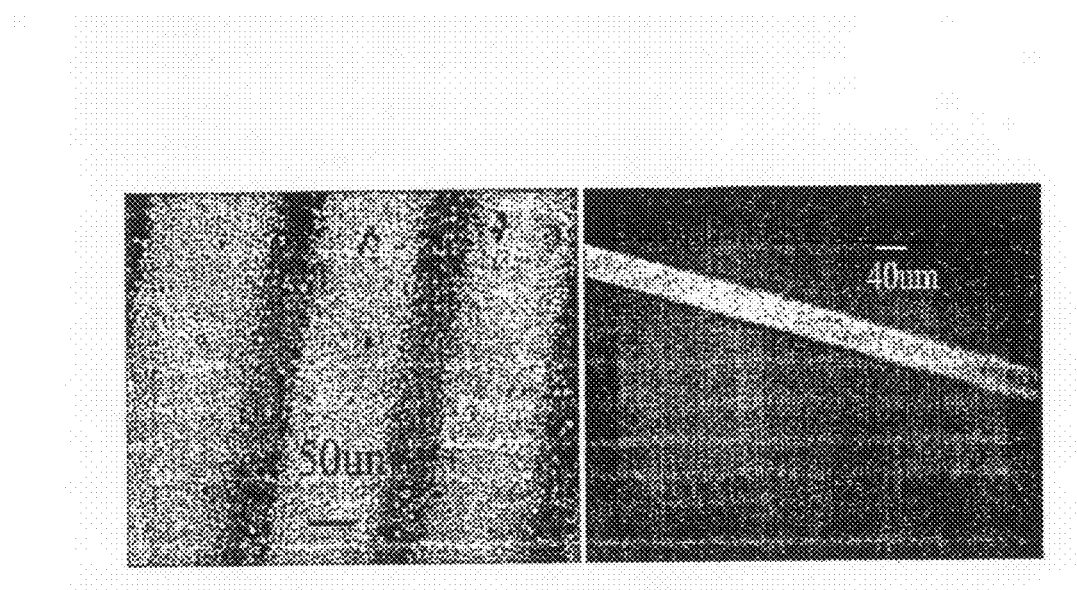
FIG. 5 is a pair of photographs demonstrating the resolution that is possible with a sophisticated laser printer as compared to an ordinary laser printer.

Another embodiment involves using a laser printer to print a negative image 400 of an electrode as shown in FIG. 4. The negative is then dipped into a conductive polymer deposition/coating system. This results in polymer coating both the negative image and the exposed substrate. Then the image is developed by removing the toner. In one example of this embodiment a negative image of an interdigitated electrode (IDE) is printed on an ordinary overhead transparency using a laser printer. The conductive polymer is formed in situ according to the following method. The transparency is immersed in a reaction system comprising 0.05 mole metanilic acid monomer, 0.05 mole aniline monomer, and 0.05 mole ammonium persulfate oxidant in 1M HCl. The reaction is kept in an ice-bath for about 2 to 3 hours while sulfonated polyaniline is being gradually deposited onto both the exposed and the toner-covered areas. The transparency is then removed and washed with DI water to quench the reaction and remove SPAN particles, which tend to accumulate. Finally, the toner is removed by sonicating in acetone for about one minute.

Figure 8:
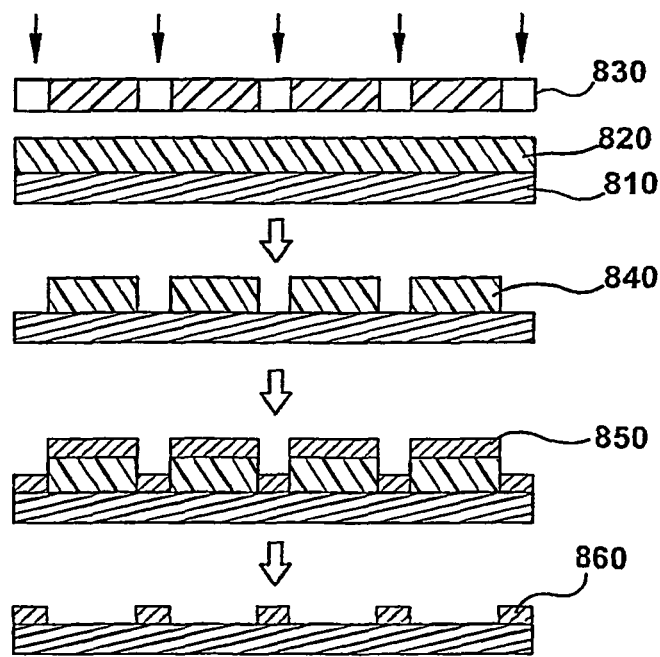
FIG. 8 is a diagram showing the steps of fabricating two dimensionally patterned electrodes by positive lithography and lift-off.

In another embodiment, electrodes of the present invention are fabricated photolithographically (FIG. 8). In one such embodiment a positive photoresist 820 is coated on a substrate 810 and exposed to UV light through a negative mask 830, thereby forming a latent image 840. The latent image is then coated with conductive pre-polymer, and cured 850. Finally, the image 860 is developed by removing the balance of the photoresist through sonication.

Masks within the scope of this embodiment can be fabricated from an ordinary overhead transparency, wherein the image is printed thereon by a laser printer capable of 20 μm line widths. Alternatively, masks within the scope of this embodiment can comprise a chromium image, which is capable of much higher resolutions including resolutions on the nanometer scale. Substrates within the scope of the present embodiment are characterized by tolerance to the aggressive chemicals and high temperatures that are often experienced in photolithographic processing. Substrates within the scope of this embodiment include, without limitation, polyimides especially the polyimide sold by DuPont under the trade name KAPTON®.

Figure 9:
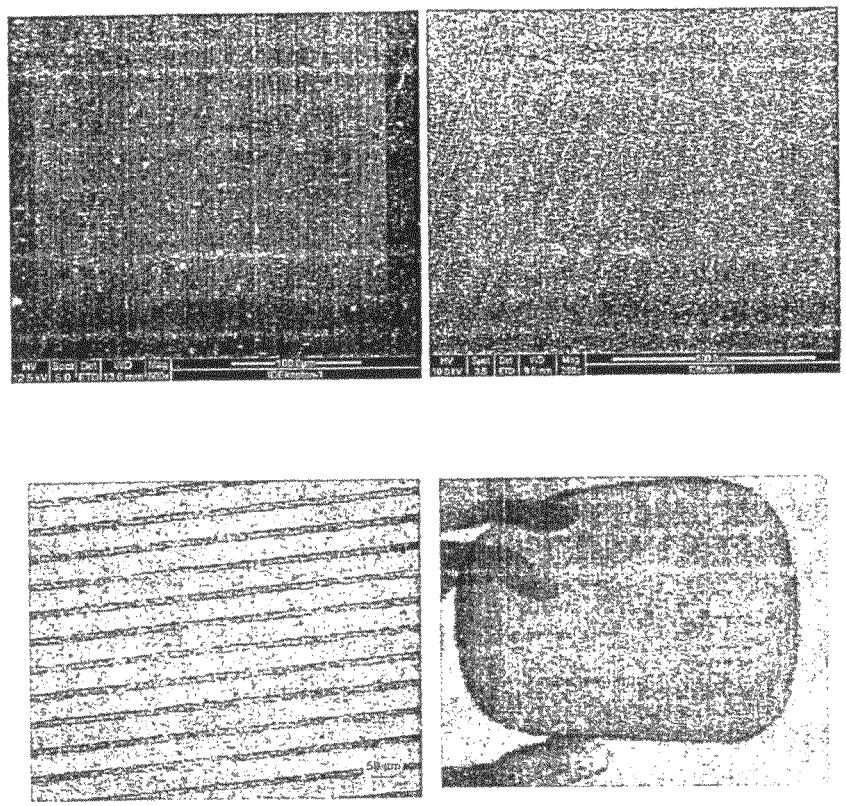
FIG. 9 is a group of images including SEMs and photographs of interdigitated electrodes made from conductive polymers using positive lithography and lift-off.

In an example of this embodiment a polyimide film is cut into 4 inch wafers and attached to a silicon wafer with double sided tape (FIG. 9, bottom right). A layer of positive photoresist is then spin coated onto the film. The photoresist is exposed to UV light under a mask comprising the negative IDE image. After 2 to 3 seconds of exposure the film is developed, flushed with DI water and dried. The film is then removed from the silicon wafer and dipped into an in situ polymerization system such as that which was described in the previous embodiment. Finally, the electrode is formed by removing the balance of the photoresist through sonicating in acetone for about one minute.

Coatings

Electrodes within the scope of the present invention can optionally include a non-conductive, electrically insulating, coating. The effect of such a coating is to shield surrounding cells and/or tissues from electric current. Thus, electrodes that include such a coating operate based on an electric field effect only, and not based on an electric current effect. Conversely, electrodes within the scope of the present invention can lack such a non-conductive, electrically insulating, coating. Electrodes that lack such a coating operate based on an electric field effect and/or an electric current effect.

Figure 14:
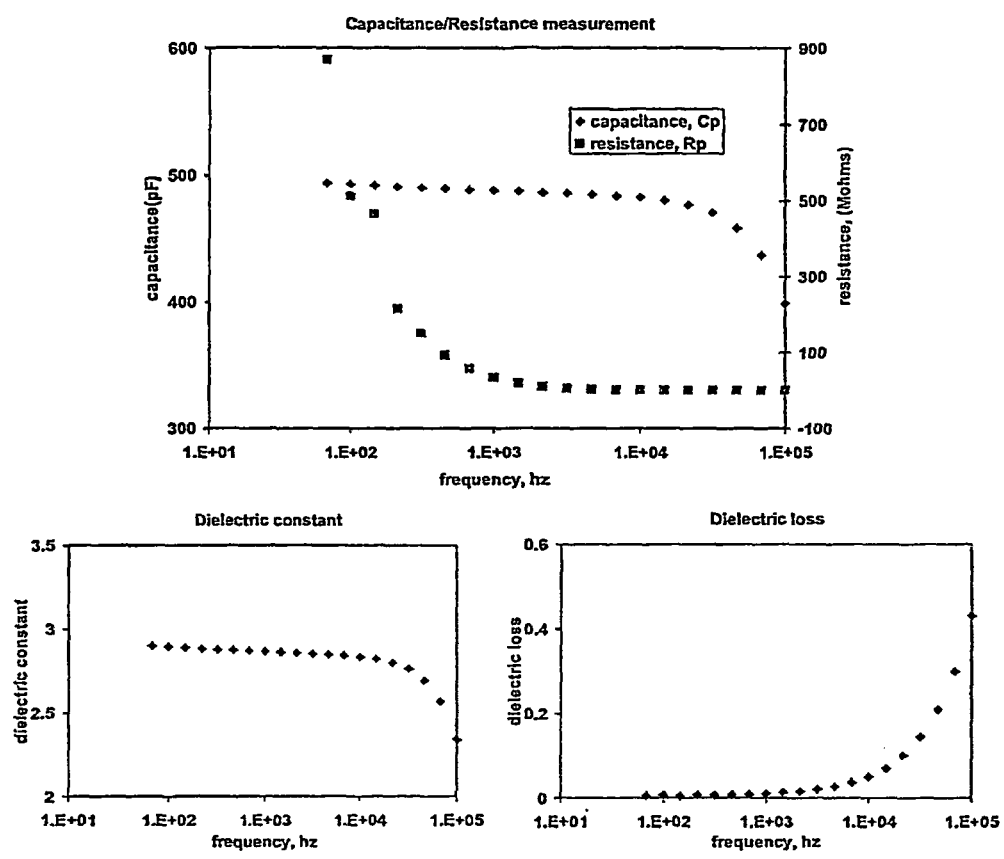
FIG. 14 is a set of graphs showing the dielectric properties of an insulating layer of PLA.

Coatings that are within the scope of the present invention include all biocompatible insulating coatings. More particularly, such coatings include, without limitation, ceramics and organic polymers. Still more particularly, such coatings include, without limitation, polylactic acid (PLA), Poly glycolide (PGA), polylactic acid-co-polyglycolide copolymer (PLGA), poly caprolactone (PCL), and polyanhydride. The dielectric properties of a PLA insulating layer is shown in FIG. 14.

Example 1

In one example of the present invention Human osteosarcoma (HOS) cells are cultured according to known methods. In this example the cells are purchased from American Type Culture Collection (ATCC, cat#CRL-1543) and cultured in the minimum essential medium sold by ATCC under the trade name EAGLE. The medium is supplemented with about 10% fetal bovine serum, and 1% antibiotics/antimycotics. Cells are maintained in a humid incubator comprising about 5% CO2 and held at about 37° C. The culture is split 1:2 every other day with 0.25% trypsin in 1 mM EDTA once confluence is reached.

Figure 10:
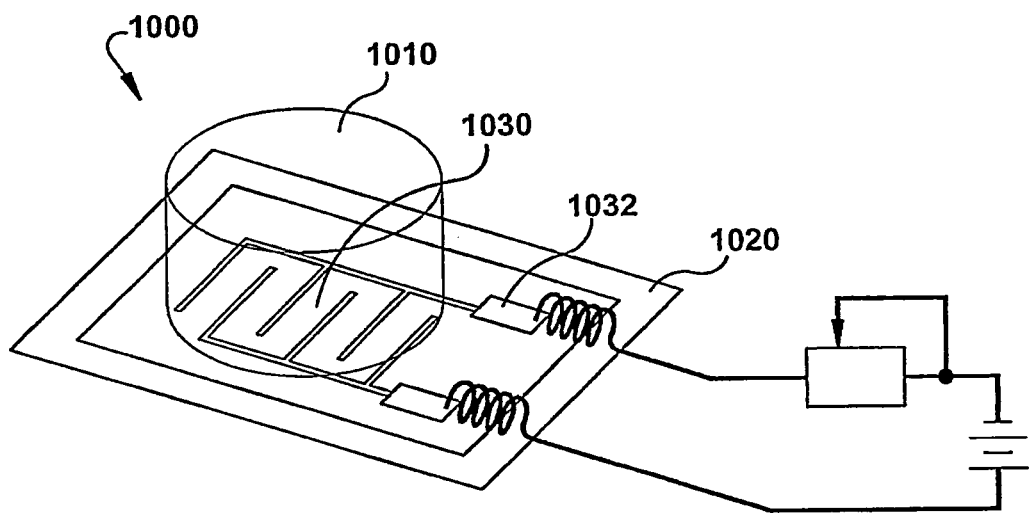
FIG. 10 is an illustration of an apparatus for electrical stimulation of bone cells on a patterned electrode.

In this example the electric field is generated by an interdigitated electrode system 1000 comprising a PLA-coated SPAN film on a nonconductive plastic substrate 1020. A plastic cylinder 1010 is bonded to the substrate 1020 with a silicone adhesive so that the interdigitated electrode 1030 is exposed to the interior volume of the cylinder 1010, as shown in FIG. 10. Thus, the electrode 1030 forms the bottom of a well, and the cylinder 1010 forms the sides. The electrode 1030 includes a portion for forming electrical contacts 1032, which connect the electrode 1030 to a power supply.

Before seeding the electrode 1030 with cells the entire well is sterilized by washing it twice with phosphate buffered saline, and then irradiating it for 30 minutes with UV light. Following this treatment, the bottom of the well is evenly seeded with trypsinized HOS cells. Additional media is added to the well as needed. The seeding density is checked with a hemocytometer and verified to be less than $2 \times 10^4$ cells per well, which is necessary in order to obtain an accurate LSC cell count in the proliferation study. The cells are cultured for 24 hours and then, are electrically stimulated for four hours using DC power (0~1V) or AC power (10~100 KHz, 0~1V). In either case, electrical stimulation is carried out inside the incubator. Following stimulation, the cells are cultured for another 24 hours. The effect of electrical stimulation on cell growth is assessed in terms of alkaline phosphatase activity, calcium deposition, and cellular proliferation as compared to an appropriate control without electrical stimulation.

In this example, alkaline phosphatase activity is determined as follows. Twenty microliters of supernatant is collected from each well, mixed with 1 mL of p-nitrophenyl phosphate, and incubated at room temperature for about 30 minutes. The activity is established by measuring the absorption at 405 nm, which is directly proportional to alkaline phosphatase activity.

In this example, calcium deposition in the extracellular matrix (ECM) is measured as follows. The media is removed from each well and 1 mL of 0.1 N HCl is added, which dissolves any calcium that may be present. After incubating at room temperature for 2 hours, 20 μL of supernatant is sampled and mixed with 1 mL of o-cresolphthalein complex. After five minutes the absorption at 575 nm is measured, and the reading is directly proportional to calcium concentration.

Figure 2:
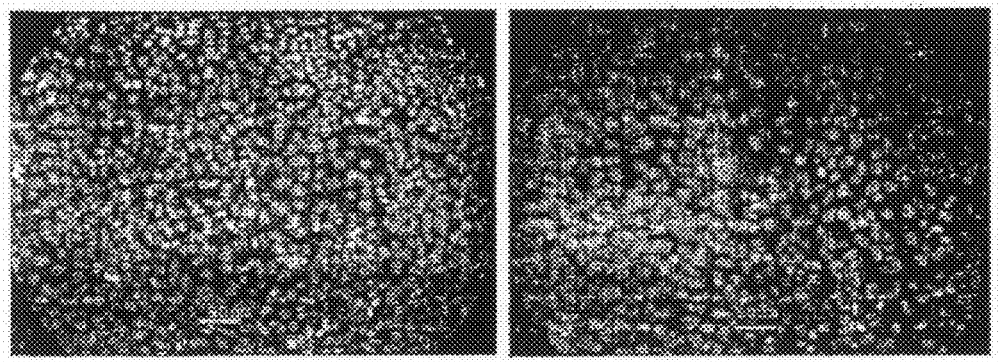
FIG. 2 is a photograph comparing cell growth on standard glass and on synthesized sulfonated polyaniline.
Figure 3:
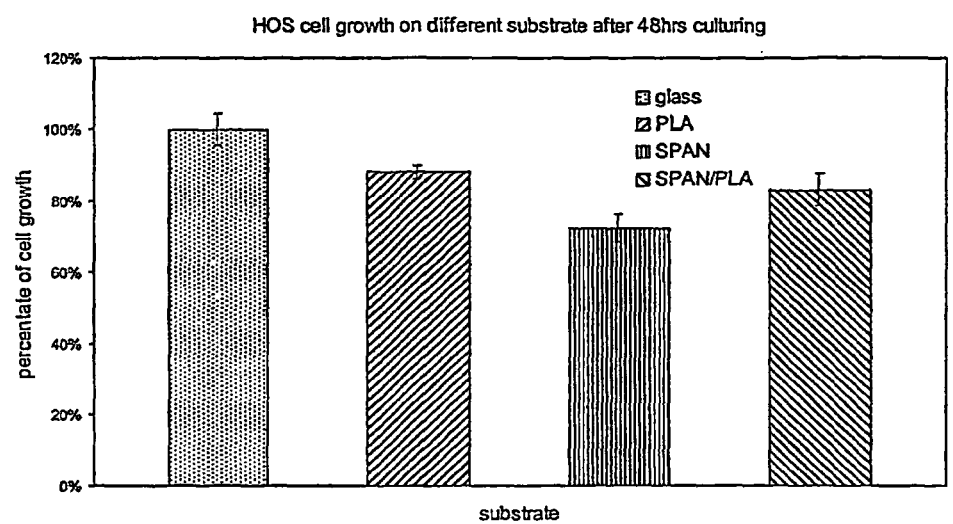
FIG. 3 is a graph showing the effect of growing cells on different substrates including non-coated sulfonated polyaniline and PLA coated polyaniline.

In this example, cellular proliferation is measured as follows. After the medium is removed, the cell layer is fixed with 70% ethanol and then stained with propidium iodide. Cells can then be observed under fluorescence using laser scanning cytometry (LSC) (see FIG. 2). Preferably at least five 1.8 mm radius areas are randomly sampled and counted. The average number of cells is thus obtained.

Example 2

In another example of the present invention one or more electrodes are surgically implanted into an animal. In this example the electrodes comprise biodegradable and/or bioabsorbable components so that the device need not be removed from the animal when it is no longer needed. More particularly, the electrode of this example comprises biodegradable CPs encased in polylactic acid). The applied potential can have any appropriate wave form, for example, sinusoidal, square, triangular or constant. Furthermore, the applied voltage may have any appropriate magnitude including 0 to 1600 mV, 50 to 1200 mV, 100 to 1000 mV, and 200 to 800 mV. In some embodiments, the resulting electric field is applied for an amount of time effective to influence cellular physiology and/or growth. This is includes embodiments where the invention effects only partial healing and/or regeneration.

The foregoing examples are considered only illustrative of the principles of the invention rather than an exclusive list of embodiments. Further, since numerous modifications and changes will readily occur to those of ordinary skill in the art, the invention is not intended to be limited to the exact construction and operation shown and described, and accordingly, all suitable modifications and equivalents are within the scope of the present invention.

What is claimed is:

1. A method for regulating cellular and tissue physiology comprising the steps of:
providing at least one patterned bioabsorbable electrode; the bioabsorbable electrode comprising a self-doped sulfonated polyanaline wherein a $SO_3H$ dopant is covalently tethered to the polyanaline;
providing at least one cell;
placing the at least one patterned bioabsorbable electrode in electrical communication with the at least one cell; and
applying a voltage to the patterned bioabsorbable electrode thereby delivering an effective amount of a patterned electric field or current to the at least one cell, whereby the patterned electric field regulates the physiology or growth of the cell.

2. The method of claim 1, wherein the patterned bioabsorbable electrode further comprises one or more of a two or three dimensionally patterned electrode.

3. The method of claim 1, wherein the pattern of the patterned bioabsorbable electrode includes one or more electrode features of interdigitated designs, parallel lines, and concentric circles.

4. The method of claim 3, wherein spacing between the electrode features is between about 10 nm and 200 pm.

5. The method of claim 3, wherein an electrical charge of each electrode feature is opposite of one or more adjacent features.

6. The method of claim 1, wherein the patterned bioabsorbable electrode is coated on a substrate comprising one or more of organic polymers, biopolymers, bioabsorbable polymers, biodegradable polymers, metal oxide glasses, and ceramics.

7. The method of claim 1, wherein the patterned bioabsorbable electrode is further characterized by a surface roughness sufficient to encourage cellular adhesion.

8. The method of claim 7, wherein the sufficient surface roughness results from adding a dielectric coating to the patterned bioabsorbable electrode.

9. The method of claim 1, wherein the dopant concentration in the self-doped sulfonated polyanaline ranges from about 0.05 to about 1.0 sulfonic acid groups per aniline repeating unit.

10. The method of claim 1, wherein subjecting the cells to a patterned electric field or current enables regulation of one or more of: stimulating cellular proliferation, healing, regeneration, ion channel function, secretory processes, chemical absorption processes, anabolic and catabolic processes, mass transport processes, cell membrane permeability, gene product production and cell division.

11. The method of claim 1, wherein the cells include one or more of: bone cells, osteoprogenitor cells, stem cells, blood cells, cardiac cells, muscle cells, nerve cells, skin cells and vascular cells.

12. The method of claim 11, wherein the cells are in vivo.

13. The method of claim 11, wherein the cells are in vitro.

14. The method of claim 1, wherein the sulfonated polyaniline is present in a leucoemeraldine oxidation state.

15. The method of claim 1, wherein the sulfonated polyaniline is present in an emeraldine oxidation state.

16. The method of claim 1, wherein the sulfonated polyaniline is present in a pemigraniline oxidation state.

17. The method of claim 1, wherein the patterned bioabsorbable electrode is present as a film on a nonconductive substrate.

18. A device for regulating cellular and tissue physiology comprising: at least one patterned bioabsorbable electrode; the bioabsorbable electrode comprising a self-doped sulfonated polyanaline wherein a $SO_3H$ dopant is covalently tethered to the polyanaline, the bioabsorbable electrode being capable of delivering an effective amount of a patterned electric field or current to a locus where dosing is indicated.

19. The device of claim 18, wherein the patterned bioabsorbable electrode is a two or three dimensionally patterned electrode.

20. The device of claim 18, wherein the patterned bioabsorbable electrode is an interdigitated electrode.

21. The device of claim 18, wherein the bioabsorbable patterned electrode is capable of producing an electric field having a field strength maximum located at a distance from the electrode producing the field.

22. The device of claim 18, wherein spacing between the electrode features is between about 10 nm and 200 pm.

23. The device of claim 18, wherein an electrical charge of each electrode feature is opposite of one or more adjacent features.

24. The device of claim 18, wherein the patterned bioabsorbable electrode is coated on a substrate comprising one or more of organic polymers, biopolymers, bioabsorbable polymers, biodegradable polymers, metal oxide glasses, and ceramics.

25. The device of claim 18, wherein the patterned bioabsorbable electrode is further characterized by a surface roughness sufficient to encourage cellular adhesion.

26. The device of claim 25, wherein the sufficient surface roughness results from adding a dielectric coating to the patterned bioabsorbable electrode.

27. The device of claim 18, wherein the dopant concentration in the self-doped sulfonated polyanaline ranges from about 0.05 to about 1.0 sulfonic acid groups per aniline repeating unit.

28. The device of claim 18, wherein the device is capable of subjecting the cells to a patterned electric field or current enables regulation of one or more of: stimulating cellular proliferation, healing, regeneration, ion channel function, secretory processes, chemical absorption processes, anabolic and catabolic processes, mass transport processes, cell membrane permeability, gene product production and cell division.

29. The device of claim 18, wherein the cells include one or more of: bone cells, osteoprogenitor cells, stem cells, blood cells, cardiac cells, muscle cells, nerve cells, skin cells and vascular cells.

30. The device of claim 29, wherein the cells are in vivo.

31. The device of claim 29, wherein the cells are in vitro.

32. The device of claim 18, wherein the sulfonated polyaniline is present in a leucoemeraldine oxidation state.

33. The device of claim 18, wherein the sulfonated polyaniline is present in an emeraldine oxidation state.

34. The device of claim 18, wherein the sulfonated polyaniline is present in a pemigraniline oxidation state.

35. The device of claim 18, wherein the patterned bioabsorbable electrode is present as a film on a nonconductive substrate.

36. A process for fabricating a patterned bioabsorbable electrode for regulating cellular and tissue physiology comprising the steps of:
providing a nonconductive substrate;
providing a bioabsorbable conductive material comprised of a self-doped sulfonated polyanaline wherein a $SO_3H$ dopant is covalently tethered to the polyanaline; and
applying the bioabsorbable conductive material to the substrate in a manner that forms a patterned conductive bioabsorbable film adhering to the substrate.

37. The process of claim 36, further comprising applying a second nonconductive substrate over the patterned conductive bioabsorbable film, and applying a bioabsorbable conductive material to the second nonconductive substrate in a manner that forms a second patterned conductive bioabsorbable film adhering to the second nonconductive substrate.

38. The process of claim 36, wherein the nonconductive substrate is selected from one or more of organic polymers, biopolymers, bioabsorbable polymers, biodegradable polymers, metal oxide glasses, and ceramics.

\* \* \* \* \*